United States Patent
Miles et al.

(10) Patent No.: US 9,795,387 B2
(45) Date of Patent: Oct. 24, 2017

(54) MEDICAL DEVICE FOR MODIFICATION OF LEFT ATRIAL APPENDAGE AND RELATED SYSTEMS AND METHODS

(71) Applicant: Coherex Medical, Inc., Salt Lake City, UT (US)

(72) Inventors: Scott D. Miles, Sandy, UT (US); Richard J. Linder, Sandy, UT (US); Clark C. Davis, Holladay, UT (US); Brian K. Whisenant, Salt Lake City, UT (US); Daryl R. Edmiston, Draper, UT (US); DeWayne C. Fox, South Jordan, UT (US)

(73) Assignee: Coherex Medical, Inc., Salt Lake City, UT (US)

( * ) Notice: Subject to any disclaimer, the term of this patent is extended or adjusted under 35 U.S.C. 154(b) by 321 days.

(21) Appl. No.: 14/487,885

(22) Filed: Sep. 16, 2014

(65) Prior Publication Data
US 2015/0066074 A1    Mar. 5, 2015

Related U.S. Application Data

(63) Continuation of application No. 12/253,831, filed on Oct. 17, 2008, now Pat. No. 8,845,711.
(Continued)

(51) Int. Cl.
*A61F 2/06* (2013.01)
*A61B 17/12* (2006.01)
(Continued)

(52) U.S. Cl.
CPC .... *A61B 17/12122* (2013.01); *A61B 17/1214* (2013.01); *A61B 17/1215* (2013.01);
(Continued)

(58) Field of Classification Search
CPC ............ A61B 17/0057; A61B 17/0469; A61B 2017/00663; A61B 2017/0472
See application file for complete search history.

(56) References Cited

U.S. PATENT DOCUMENTS

| | | |
|---|---|---|
| 3,095,877 A | 7/1963 | Rowan |
| 3,874,388 A | 4/1975 | King et al. |

(Continued)

FOREIGN PATENT DOCUMENTS

| | | |
|---|---|---|
| CA | 2627408 | 5/2008 |
| DE | 102006056283 | 6/2008 |

(Continued)

OTHER PUBLICATIONS

English Abstract and English machine translation of the Specification and Claims of DE102006056283. Jun. 5, 2008.
(Continued)

*Primary Examiner* — Gregory Anderson
(74) *Attorney, Agent, or Firm* — David L. Stott

(57) ABSTRACT

Several embodiments are set forth of devices, systems and methods for modifying an atrial appendage such as a left atrial appendage (LAA). In one embodiment, a medical device includes a frame member and a tissue growth member. The frame member includes a unitary, seamless central portion having a plurality of struts defining a multi-cellular structure and an anchoring system, the plurality of struts extending between and configured to self-expand and directly bias the anchor system to anchor the frame member at least partially within the LAA. With this arrangement, the tissue growth member is attached to the frame member to occlude the LAA.

13 Claims, 18 Drawing Sheets

Related U.S. Application Data

(60) Provisional application No. 60/981,451, filed on Oct. 19, 2007.

(51) Int. Cl.
*A61B 17/00* (2006.01)
*A61B 17/04* (2006.01)
*A61B 17/064* (2006.01)

(52) U.S. Cl.
CPC .... *A61B 17/1219* (2013.01); *A61B 17/12022* (2013.01); *A61B 17/12159* (2013.01); *A61B 17/12172* (2013.01); *A61B 17/12186* (2013.01); *A61B 17/00491* (2013.01); *A61B 2017/00243* (2013.01); *A61B 2017/00898* (2013.01); *A61B 2017/0412* (2013.01); *A61B 2017/0427* (2013.01); *A61B 2017/0649* (2013.01); *A61B 2017/1205* (2013.01)

(56) References Cited

U.S. PATENT DOCUMENTS

| | | |
|---|---|---|
| 5,171,259 A | 12/1992 | Inoue |
| 5,192,301 A | 3/1993 | Kamiya et al. |
| 5,284,488 A | 2/1994 | Sideris |
| 5,334,217 A | 8/1994 | Das |
| 5,425,733 A | 6/1995 | Schmieding |
| 5,425,740 A | 6/1995 | Hutchinson, Jr. |
| 5,433,727 A | 7/1995 | Sideris |
| 5,792,165 A | 8/1998 | Klieman et al. |
| 5,861,003 A | 1/1999 | Latson et al. |
| 5,904,703 A | 5/1999 | Gilson |
| 5,910,154 A | 6/1999 | Tsugita et al. |
| 5,992,158 A | 11/1999 | Goddard et al. |
| 6,152,144 A | 11/2000 | Lesh et al. |
| 6,174,322 B1 | 1/2001 | Schneidt |
| 6,231,561 B1 | 5/2001 | Frazier et al. |
| 6,238,403 B1 | 5/2001 | Greene et al. |
| 6,290,674 B1 | 9/2001 | Roue et al. |
| 6,328,727 B1 | 12/2001 | Frazier et al. |
| 6,355,051 B1 | 3/2002 | Sisskind et al. |
| 6,371,971 B1 | 4/2002 | Tsugita et al. |
| 6,398,760 B1 | 6/2002 | Danby |
| 6,419,669 B1 | 7/2002 | Frazier et al. |
| 6,436,088 B2 | 8/2002 | Frazier et al. |
| 6,458,100 B2 | 10/2002 | Roue et al. |
| 6,488,689 B1 | 12/2002 | Kaplan et al. |
| 6,530,934 B1 | 3/2003 | Jacobsen et al. |
| 6,551,303 B1 | 4/2003 | Van Tassel et al. |
| 6,551,341 B2 | 4/2003 | Boylan et al. |
| 6,561,969 B2 | 5/2003 | Frazier et al. |
| 6,641,557 B1 | 11/2003 | Frazier et al. |
| 6,650,923 B1 | 11/2003 | Lesh et al. |
| 6,652,555 B1 | 11/2003 | VanTassel et al. |
| 6,652,556 B1 | 11/2003 | VanTassel et al. |
| 6,666,861 B1 | 12/2003 | Grabek |
| 6,689,150 B1 | 2/2004 | VanTassel et al. |
| 6,702,825 B2 | 3/2004 | Frazier et al. |
| 6,706,065 B2 | 3/2004 | Langberg et al. |
| 6,712,804 B2 | 3/2004 | Roue et al. |
| 6,730,108 B2 | 5/2004 | Van Tassel et al. |
| 6,746,472 B2 | 6/2004 | Frazier et al. |
| 6,790,229 B1 | 9/2004 | Berreklouw |
| 6,949,113 B2 | 9/2005 | Van Tassel et al. |
| 6,979,344 B2 | 12/2005 | Jones et al. |
| 6,994,092 B2 | 2/2006 | van der Burg et al. |
| 7,011,671 B2 | 3/2006 | Welch |
| 7,014,645 B2 | 3/2006 | Greene, Jr. et al. |
| 7,025,756 B2 | 4/2006 | Frazier et al. |
| 7,044,134 B2 | 5/2006 | Khairkhahan et al. |
| 7,056,294 B2 | 6/2006 | Khairkhahan et al. |
| 7,115,110 B2 | 10/2006 | Frazier et al. |
| 7,128,073 B1 | 10/2006 | van der Burg et al. |
| 7,152,605 B2 | 12/2006 | Khairkhahan et al. |
| 7,169,164 B2 | 1/2007 | Borillo et al. |
| 7,192,439 B2 | 3/2007 | Khairkhahan et al. |
| 7,226,458 B2 | 6/2007 | Kaplan et al. |
| 7,293,562 B2 | 11/2007 | Malecki et al. |
| 7,597,704 B2 | 10/2009 | Frazier et al. |
| 7,608,091 B2 | 10/2009 | Goldfarb et al. |
| 7,717,937 B2 | 5/2010 | Wahr et al. |
| 7,727,189 B2 | 6/2010 | VanTassel et al. |
| 7,780,645 B2 | 8/2010 | Jones |
| 7,842,054 B2 | 11/2010 | Greene, Jr. et al. |
| 8,142,470 B2 | 3/2012 | Quinn et al. |
| 8,740,934 B2 | 6/2014 | McGuckin, Jr. |
| 2001/0003161 A1 | 6/2001 | Vardi et al. |
| 2001/0037141 A1 | 11/2001 | Yee et al. |
| 2002/0022860 A1 | 2/2002 | Borillo et al. |
| 2002/0026094 A1 | 2/2002 | Roth |
| 2002/0026217 A1 | 2/2002 | Baker et al. |
| 2002/0062130 A1 | 5/2002 | Jugenheimer et al. |
| 2002/0177855 A1 | 11/2002 | Greene, Jr. et al. |
| 2002/0183787 A1 | 12/2002 | Wahr et al. |
| 2003/0014075 A1 | 1/2003 | Rosenbluth et al. |
| 2003/0055455 A1 | 3/2003 | Yang et al. |
| 2003/0057156 A1 | 3/2003 | Peterson et al. |
| 2003/0120337 A1 | 6/2003 | Van Tassel et al. |
| 2003/0125790 A1 | 7/2003 | Fastovsky et al. |
| 2003/0171739 A1 | 9/2003 | Murphy et al. |
| 2003/0181942 A1 | 9/2003 | Sutton et al. |
| 2003/0187474 A1 | 10/2003 | Keegan et al. |
| 2003/0191526 A1 | 10/2003 | Van Tassel et al. |
| 2003/0195555 A1 | 10/2003 | Khairkhahan et al. |
| 2003/0199923 A1 | 10/2003 | Khairkhahan et al. |
| 2003/0204203 A1 | 10/2003 | Khairkhahan et al. |
| 2003/0212432 A1 | 11/2003 | Khairkhahan et al. |
| 2003/0220667 A1 | 11/2003 | Van Der Burg et al. |
| 2004/0034366 A1 | 2/2004 | Van Der Burg et al. |
| 2004/0049224 A1 | 3/2004 | Buehlmann et al. |
| 2004/0098028 A1 | 5/2004 | Martinez |
| 2004/0122467 A1 | 6/2004 | VanTassel et al. |
| 2004/0127935 A1 | 7/2004 | VanTassel et al. |
| 2004/0153120 A1 | 8/2004 | Seifert et al. |
| 2004/0215230 A1 | 10/2004 | Frazier et al. |
| 2004/0254594 A1 | 12/2004 | Alfaro |
| 2004/0260317 A1 | 12/2004 | Bloom et al. |
| 2004/0267191 A1 | 12/2004 | Gifford, III et al. |
| 2005/0004652 A1 | 1/2005 | van der Burg et al. |
| 2005/0033409 A1 | 2/2005 | Burke et al. |
| 2005/0038470 A1 | 2/2005 | Van Der Burg et al. |
| 2005/0043759 A1 | 2/2005 | Chanduszko |
| 2005/0049573 A1 | 3/2005 | Van Tassel et al. |
| 2005/0049681 A1 | 3/2005 | Greenhalgh et al. |
| 2005/0060017 A1 | 3/2005 | Fishell et al. |
| 2005/0065589 A1 | 3/2005 | Schneider et al. |
| 2005/0075665 A1 | 4/2005 | Brenzel et al. |
| 2005/0090860 A1 | 4/2005 | Paprocki |
| 2005/0113861 A1 | 5/2005 | Corcoran et al. |
| 2005/0149173 A1 | 7/2005 | Hunter et al. |
| 2005/0177182 A1 | 8/2005 | van der Burg et al. |
| 2005/0192616 A1 | 9/2005 | Callister et al. |
| 2005/0192627 A1 | 9/2005 | Whisenant et al. |
| 2005/0222533 A1 | 10/2005 | Chanduszko et al. |
| 2005/0234540 A1 | 10/2005 | Peavey et al. |
| 2005/0234543 A1 | 10/2005 | Glaser et al. |
| 2005/0251144 A1 | 11/2005 | Wilson et al. |
| 2005/0256532 A1 | 11/2005 | Nayak et al. |
| 2005/0267524 A1 | 12/2005 | Chanduszko |
| 2006/0000443 A1 | 1/2006 | Kado et al. |
| 2006/0004433 A1 | 1/2006 | Greenberg et al. |
| 2006/0009798 A1 | 1/2006 | Callister |
| 2006/0009800 A1 | 1/2006 | Christianson et al. |
| 2006/0036282 A1 | 2/2006 | Wahr et al. |
| 2006/0052816 A1 | 3/2006 | Bates et al. |
| 2006/0122646 A1 | 6/2006 | Corcoran et al. |
| 2006/0149299 A1 | 7/2006 | Greene et al. |
| 2006/0149307 A1 | 7/2006 | Durgin |
| 2006/0149314 A1 | 7/2006 | Borillo et al. |
| 2006/0155323 A1 | 7/2006 | Porter et al. |
| 2006/0206148 A1 | 9/2006 | Khairkhahan et al. |
| 2006/0217761 A1 | 9/2006 | Opolski |
| 2006/0229668 A1 | 10/2006 | Prestezog et al. |
| 2006/0276839 A1 | 12/2006 | McGuckin, Jr. |

(56) References Cited

U.S. PATENT DOCUMENTS

| | | |
|---|---|---|
| 2007/0027456 A1 | 2/2007 | Gartner et al. |
| 2007/0066993 A1 | 3/2007 | Kreidler |
| 2007/0073247 A1 | 3/2007 | Ewaschuk |
| 2007/0083230 A1 | 4/2007 | Javois |
| 2007/0083232 A1 | 4/2007 | Lee |
| 2007/0088388 A1 | 4/2007 | Opolski et al. |
| 2007/0112382 A1 | 5/2007 | Thill et al. |
| 2007/0123934 A1 | 5/2007 | Whisenant et al. |
| 2007/0129753 A1 | 6/2007 | Quinn et al. |
| 2007/0129757 A1 | 6/2007 | Armstrong |
| 2007/0135826 A1 | 6/2007 | Zaver et al. |
| 2007/0149995 A1 | 6/2007 | Quinn et al. |
| 2007/0167981 A1 | 7/2007 | Opolski et al. |
| 2007/0173885 A1 | 7/2007 | Cartier et al. |
| 2007/0179527 A1 | 8/2007 | Eskuri et al. |
| 2007/0179583 A1 | 8/2007 | Goetzinger et al. |
| 2007/0191884 A1 | 8/2007 | Eskridge et al. |
| 2007/0198059 A1 | 8/2007 | Patel et al. |
| 2007/0213766 A1 | 9/2007 | Ravikumar |
| 2007/0237720 A1 | 10/2007 | Padilla et al. |
| 2007/0270891 A1 | 11/2007 | McGuckin |
| 2007/0276415 A1 | 11/2007 | Kladakis et al. |
| 2008/0039929 A1 | 2/2008 | Davis et al. |
| 2008/0119891 A1 | 5/2008 | Miles et al. |
| 2008/0215086 A1 | 9/2008 | Olsen et al. |
| 2009/0025820 A1 | 1/2009 | Adams |
| 2009/0069840 A1 | 3/2009 | Hallisey |
| 2009/0099596 A1 | 4/2009 | McGuckin, Jr. et al. |
| 2009/0105747 A1 | 4/2009 | Chanduszko et al. |
| 2009/0112249 A1 | 4/2009 | Miles et al. |
| 2009/0171386 A1 | 7/2009 | Amplatz et al. |
| 2009/0192518 A1 | 7/2009 | Golden et al. |
| 2009/0299338 A1 | 12/2009 | di Palma |
| 2009/0318948 A1 | 12/2009 | Linder et al. |
| 2010/0191279 A1 | 7/2010 | Kassab et al. |
| 2010/0228279 A1 | 9/2010 | Miles et al. |
| 2010/0228285 A1 | 9/2010 | Miles et al. |
| 2010/0234878 A1 | 9/2010 | Hruska et al. |
| 2010/0324585 A1 | 12/2010 | Miles et al. |
| 2010/0324586 A1 | 12/2010 | Miles et al. |
| 2010/0324587 A1 | 12/2010 | Miles et al. |
| 2010/0324588 A1 | 12/2010 | Miles et al. |
| 2011/0022079 A1 | 1/2011 | Miles et al. |
| 2011/0046658 A1 | 2/2011 | Connor et al. |
| 2011/0054515 A1 | 3/2011 | Bridgeman et al. |
| 2011/0208233 A1 | 8/2011 | McGuckin, Jr. et al. |
| 2012/0316584 A1 | 12/2012 | Miles et al. |

FOREIGN PATENT DOCUMENTS

| | | |
|---|---|---|
| EP | 1266630 | 12/2002 |
| EP | 1358850 | 11/2003 |
| EP | 1523957 | 4/2005 |
| EP | 1741393 | 1/2007 |
| JP | 2008536620 | 9/2008 |
| JP | 2010500917 | 1/2010 |
| WO | 99/33402 | 7/1999 |
| WO | 00/27292 | 5/2000 |
| WO | 01/93920 | 12/2001 |
| WO | 02/071977 | 9/2002 |
| WO | 03/028802 | 4/2003 |
| WO | 2004045393 | 6/2004 |
| WO | 2004/100803 | 11/2004 |
| WO | 2005053547 | 6/2005 |
| WO | 2005099365 | 10/2005 |
| WO | 2006/033641 | 3/2006 |
| WO | 2006047748 | 5/2006 |
| WO | 2007/054116 | 5/2007 |
| WO | 2007054116 | 5/2007 |
| WO | 2007/147145 | 12/2007 |
| WO | WO 2008/150346 | 12/2008 |
| WO | 2010/081033 | 7/2010 |
| WO | 2010/148246 | 12/2010 |

OTHER PUBLICATIONS

Office Action and English Translation issued in JP2012-516313 dated Mar. 25, 2014.
International Search Report dated Feb. 7, 2013 for International Application No. PCT/US2012/063074 (5 pages).
International Search Report dated Apr. 26, 2010 for International Application No. PCT/US2010/020549 (7 pages).
International Search Report dated May 7, 2010 for International Application No. PCT/US2010/020547 (4 pages).
International Search Report dated May 6, 2010 for International Application No. PCT/US2010/020539 (5 pages).
International Search Report dated Jun. 15, 2009 for International Application No. PCT/US2008/080374 (7 pages).

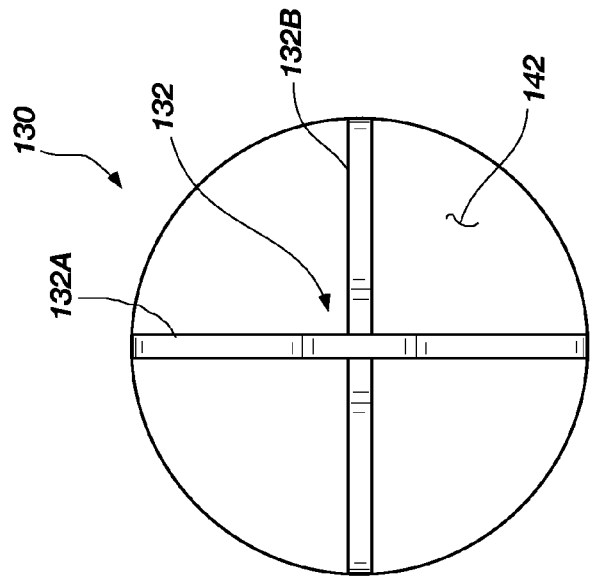
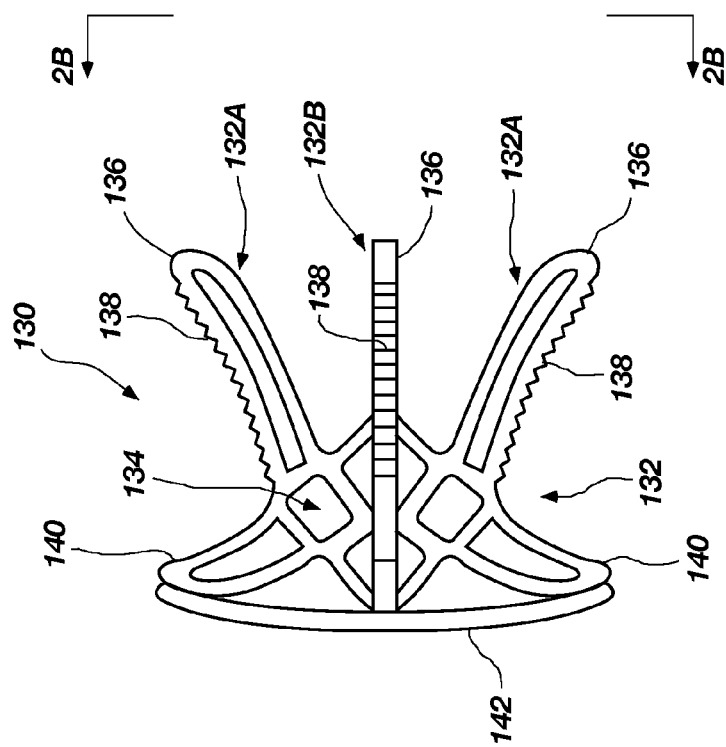

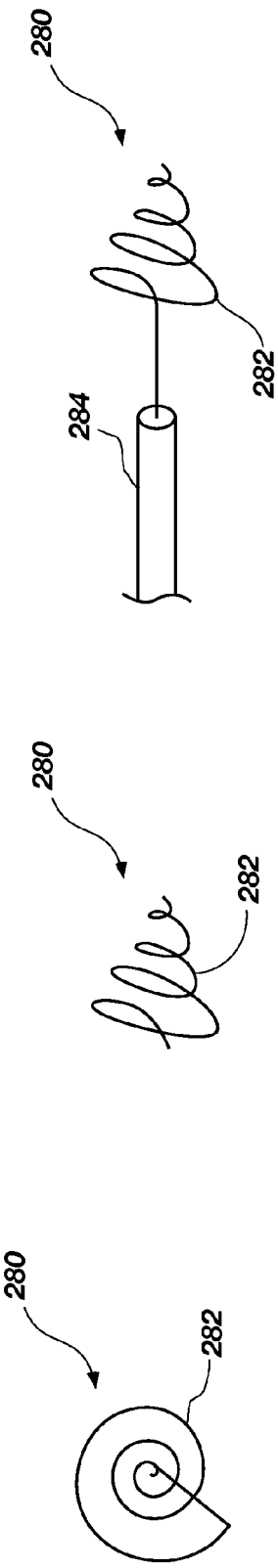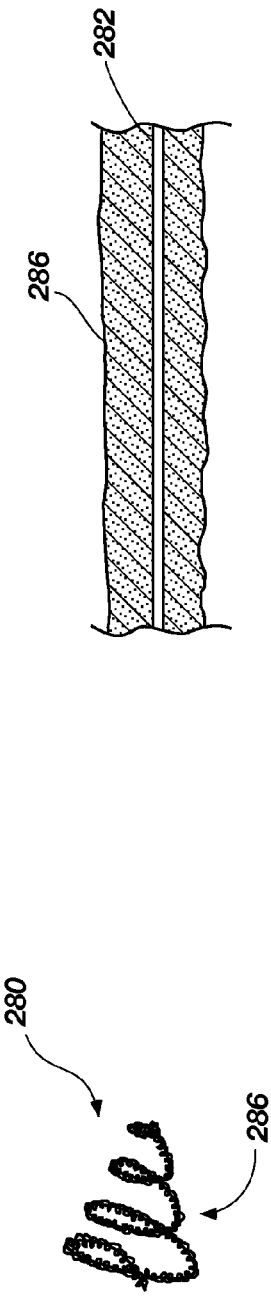
FIG. 13A  FIG. 13B  FIG. 13C  FIG. 13D  FIG. 13E

MEDICAL DEVICE FOR MODIFICATION OF LEFT ATRIAL APPENDAGE AND RELATED SYSTEMS AND METHODS

CROSS-REFERENCE TO RELATED APPLICATION

This application is a continuation application of U.S. patent application Ser. No. 12/253,831, filed Oct. 17, 2008, now U.S. Pat. No. 8,845,711, which application claims the benefit of U.S. Provisional Patent Application Ser. No. 60/981,451, filed Oct. 19, 2007, entitled MEDICAL DEVICE FOR MODIFICATION OF LEFT ATRIAL APPENDAGE, and of U.S. Provisional Application Ser. No. 61/047,058 filed Apr. 22, 2008 entitled DEVICE AND SYSTEM FOR ANEURYSM EMBOLIZATION, the disclosure of each of which is incorporated by reference herein in their entireties.

TECHNICAL FIELD

The present invention relates generally to the modification of a left atrial appendage and, more specifically, to devices, systems and methods for occluding or otherwise structurally altering such appendages.

BACKGROUND

The left atrial appendage is a feature of all human hearts. The upper chambers of the heart, the atria, have this appendage attached to each of them. The physiologic function of such appendages is not completely understood, but they do act as a filling reservoir during the normal pumping of the heart. The appendages typically protrude from the atria and cover an external portion of the atria. Atrial appendages differ substantially from one to another. For example, one atrial appendage may be configured as a tapered protrusion while another atrial appendage may be configured as a re-entrant, sock-like hole. The inner surface of an appendage is conventionally trabeculated with cords of muscular cardiac tissue traversing its surface.

The atrial appendages are inert while blood is being pumped through them during normal heart function. In other words, the appendages don't have a noticeable effect on blood pumped through them during normal heart function. However, in cases of atrial fibrillation, when the atria go into arrhythmia, blood may pool and thrombose inside of the appendages. Among other things, this can pose a stroke risk when it occurs in the left appendage since the thrombus may be pumped out of the heart and into the cranial circulation.

Historically, appendages have sometimes been modified surgically to reduce the risk imposed by atrial fibrillation. In recent years devices which may be delivered percutaneously into the left atrial appendage have been introduced. The basic function of these devices is to exclude the volume within the appendage with an implant which then allows blood within the appendage to safely thrombose and then to be gradually incorporated into cardiac tissue. This can leave a smooth, endothelialized surface where the appendage used to be.

BRIEF SUMMARY OF THE INVENTION

Embodiments of the present invention include percutaneously delivered implants or medical devices designed to exclude or modify the inner surface of the left atrial appendage to reduce the risk of stroke during atrial fibrillation. Embodiments of the present invention further include related methods and systems.

In accordance with one embodiment of the present invention, a medical device for modifying a left atrial appendage (LAA) is provided. The medical device includes a body formed of a self-expanding material. The body exhibits a textured surface including a plurality of protruding portions and a plurality of recesses. Each protruding portion is separated from an adjacent protruding portion by a recess of the plurality of recesses. In one embodiment, the body may exhibit a substantially spherical geometry. The body may be formed from a material that comprises, for example, a reticulated foam.

In accordance with another embodiment of the present invention, a medical device for modifying a left atrial appendage includes a mesh bag and at least one self-expanding body disposed within the mesh bag. The self-expanding body may include one or more foam bodies. The mesh bag may be formed of, for example, a material comprising at least one nylon, polyester or silicone. The self-expanding body or bodies may be formed of, for example, at least one of a polymer foam, polyurethane, and polyvinyl acetate.

In accordance with another embodiment of the present invention, a method of modifying a left atrial appendage is provided. The method includes providing a body formed of a self-expanding material, the body exhibiting a textured surface including a plurality of protruding portions and a plurality of recesses, wherein each protruding portion is separated from an adjacent protruding portion by a recess of the plurality of recesses. The body is compressed within a delivery vehicle and the delivery vehicle is positioned adjacent an opening of the LAA. The body is discharged from the delivery vehicle into the LAA and expanded such that the body engages a side wall of the LAA and substantially occludes an opening of the LAA.

In accordance with yet another embodiment of the present invention, another method is provided for modifying a left atrial appendage. The method includes disposing a mesh bag within the LAA and disposing at least one self-expanding body within an interior of the mesh bag. The mesh bag is securely closed to retain the at least one self-expanding body within the bag.

In another one embodiment, the medical device includes a first frame member, a second frame member, a spring member and a tissue in-growth member. The first and second frame members include a first and second flat configuration, respectively, and are non-coplanar with each other. The first frame member is configured to anchor within the left atrial appendage (LAA). The spring member is connected between the first and second frame members. The tissue in-growth member is attached to the second frame member and is configured to cover an opening of the LAA.

In a further embodiment, the medical device includes a frame member having a substantially flat configuration and includes distal anchor members for anchoring the frame member within the LAA. The medical device also includes a tissue in-growth member that is attached to the frame member and configured to cover an opening of the LAA.

In yet another embodiment, the medical device includes a frame member having an anchoring system that is configured to anchor the frame member at least partially within the LAA. The medical device also includes a tissue in-growth member that is attached to the frame member and is configured to prevent potential embolic material from escaping the LAA.

These and other aspects of the present invention will become more fully apparent from the following description and appended claims, or may be learned by the practice of the invention as set forth hereinafter.

BRIEF DESCRIPTION OF THE SEVERAL VIEWS OF THE DRAWINGS

The foregoing and other advantages of the invention will become apparent upon reading the following detailed description and upon reference to the drawings in which:

FIGS. 2A, 2B and 2C are side, end and perspective views, respectively, of another medical device according to an embodiment of the present invention;

FIGS. 13A through 13E show variations of a medical device according to additional embodiments of the present invention;

DETAILED DESCRIPTION OF SEVERAL EMBODIMENTS OF THE INVENTION

Figure 1A:
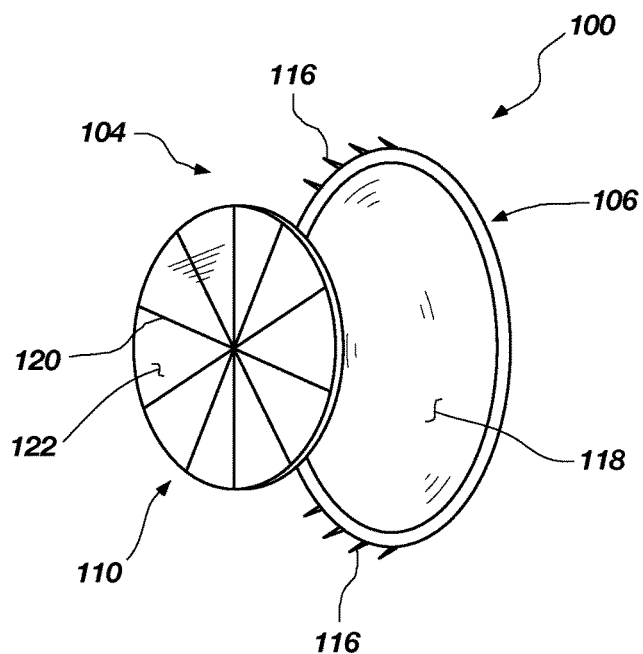
FIGS. 1A and 1B are perspective and side views of a medical device according to one embodiment of the present invention.
Figure 1B:
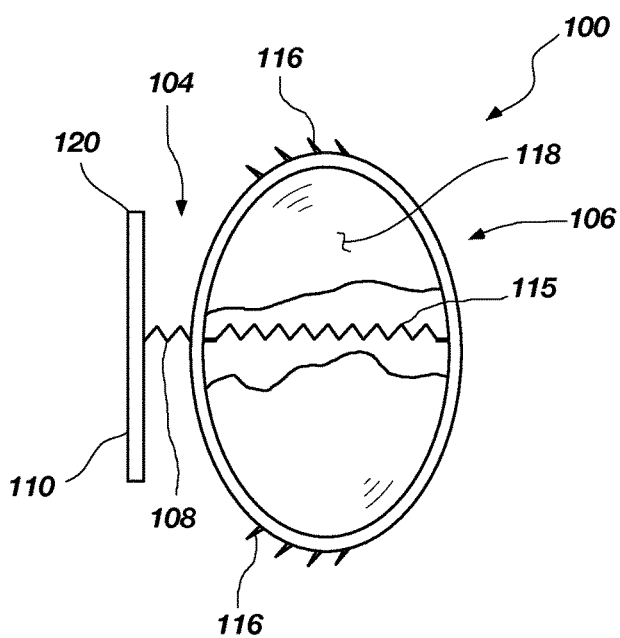
Figure 1C:
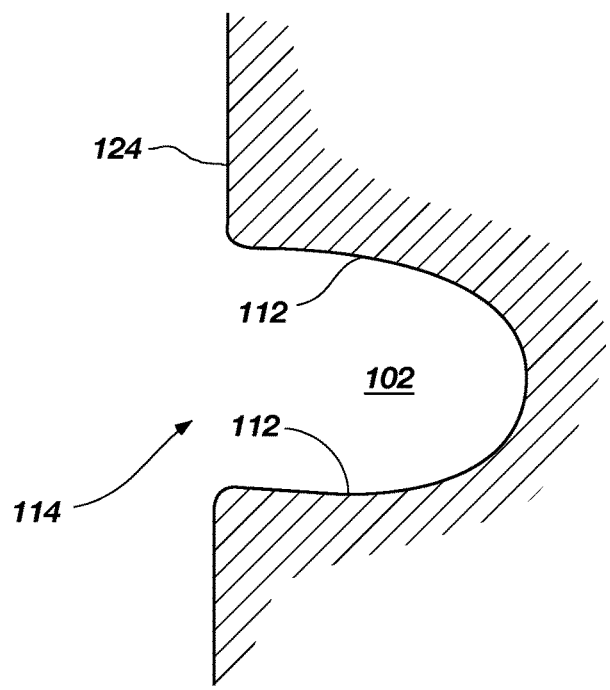
FIG. 1C illustrates an example of an atrial appendage.
Figure 1D:
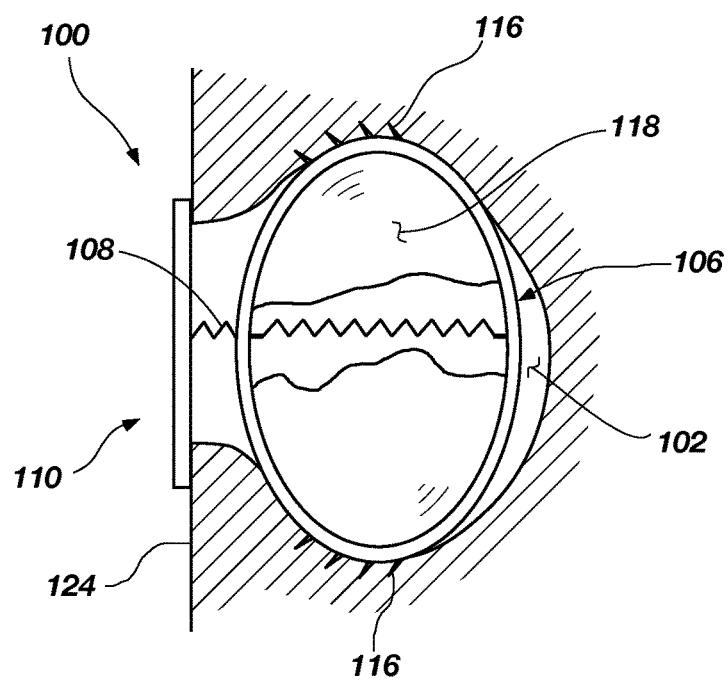
FIG. 1D shows the device of FIGS. 1A and 1B disposed in an atrial appendage.

Referring to FIGS. 1A through 1D, a medical device 100 is shown that may be used to occlude or modify an opening or cavity such as a left atrial appendage (LAA) 102 (FIGS. 1C and 1D). The medical device 100 includes a frame 104 having a distal anchoring portion or anchor member 106, a spring or biasing member 108 and a proximal cover portion or cover member 110. It is noted that the use of terms such as "distal," "proximal," "upper," and "lower" and other relative terms are used in particular reference to the drawings and such use is not to be construed as limiting with regard to absolute positions of various components described and discussed herein.

The anchor member 106 may be sized and configured to expand outward against a surface of a wall 112 of the LAA 102 so that upper and lower portions of the anchor member 106 extend to a dimension that is larger than the LAA opening 114. The anchor member 106 can be formed of, for example, a shape memory alloy such as Nitinol. Use of such a material enables the anchor member 106 to be delivered in a collapsed state and then self-expand upon deployment in the LAA 102. In another embodiment, the anchor member 106 may be configured to be manually expanded upon delivery to and deployment in the LAA 102. In one embodiment, a spring or biasing member 115 may be positioned within the anchor member 106 so as to pull opposing distal and proximal sides of the anchor member 106 towards one another such the upper and lower portions of the anchor member 106 are placed in, and maintained in, an expanded or extended position.

A plurality of tines 116, which may include, for example, posts or barbs, may be disposed on the anchor member 106. The tines 116 may be located and configured to "grab" or otherwise engage the LAA wall 112. With such an arrangement, the anchor member 106 is configured to be positioned and anchored within the LAA 102 to prevent migration of the medical device 100 out of the LAA 102. In one embodiment, the anchor member 106 may be substantially flat and planar. The anchor member 106 may also include a tissue in-growth member 118 associated therewith, such as a polymer substrate, or any suitable known member for promoting tissue growth. According to one aspect of the present invention, the tissue in-growth member can be a porous polymer member, such as a polymer based foam or fabric. In one embodiment, fabric may be disposed over the frame of the anchor member 106. In another embodiment a foam member may be disposed on or within the frame of the anchor member 106.

The cover member 110 is connected to the anchor member 106 via the biasing member 108. The cover member 110 may include a frame 120 sized and configured to be larger than the opening 114 of the LAA 102. The frame 120 can be configured to support a tissue in-growth member 122, such as a polymer substrate, or any suitable tissue promoting or enhancing member. Such tissue in-growth member 122 can be a porous member, such as reticulated foam, fabric or Dacron®, configured to hold blood cells and to promote and induce tissue growth. With the cover member 110 being coupled with the anchor member 106 via the biasing member 108, the cover member 110 can be configured to be biased against the left atrial wall 124 over the opening 114 of the LAA 102 via the biasing member 108 after the anchor member 106 is appropriately positioned and anchored within the LAA 102.

When deployed within the LAA 102, the medical device 100 covers or occludes the opening 114 of the LAA to seal off the LAA 102 from the left atria. Thus, if any embolic material exists within the LAA 102, the medical device 100 prevents such from leaving the LAA 102 and entering back into the left atria. Additionally, the medical device prevents further entry of blood into the LAA 102 and, thus, further preventing production of embolic material within the LAA.

Figure 2C:
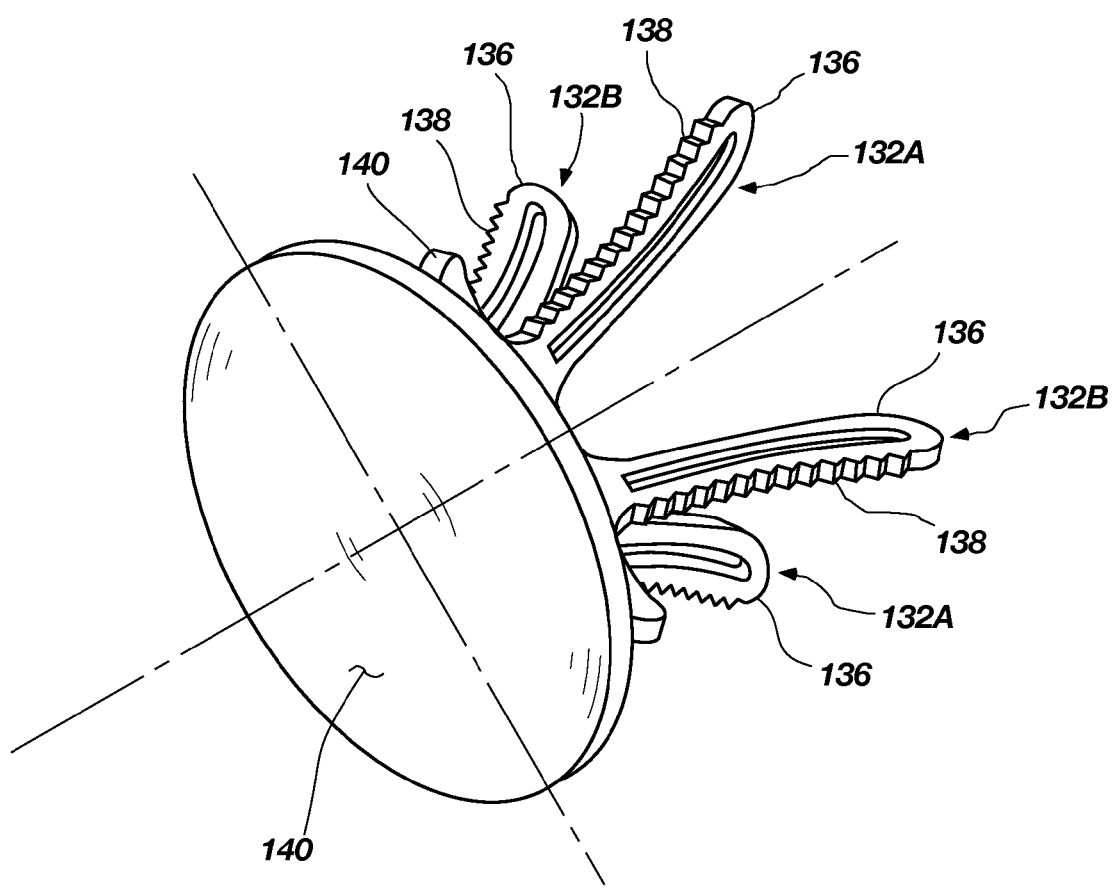

Referring now to FIGS. 2A through 2C, another medical device 130 is shown which is configured to be anchored within and occlude a cavity such as an LAA 102 (FIG. 1C). The medical device 130 may include a multi-planar structure 132 sized and configured to be anchored within the LAA 102. The multi-planar structure 132 may be formed of individual planar structures 132A and 132B arranged to extend in separate planes. Each planar structure 132A and 132B can include a central frame portion 134 having a multi-cellular structure with distal anchors 136 extending therefrom, the anchors 136 being sized, located and configured to engage the LAA wall 112 and anchor the medical device 130 therein. Further, each planar structure 132A and 132B may be self-expanding to facilitate the deployment of the distal anchors 136 and engagement with the LAA wall 112. Such anchoring can be further facilitated with tines 138 extending from the distal anchors 136 to grab or more affirmatively engage the tissue wall 112 of the LAA 102. The multi-planar structure 132 provides anchors in multiple planes to ensure the medical device 130 is secured within the LAA 102. In addition, each planar structure 132A and 132B may include proximal anchors 140 extending from the central frame portion 134. The proximal anchors 140 may be configured to extend around the outer rim of the opening 114 of the LAA 102 so as to be seated and biased against the left atrial wall 124. The proximal anchors 140 may be coupled to a polymer substrate 142 or may be covered by a suitable tissue in-growth member that may cover the opening 114 of the LAA 102 such as has been previously described above.

Figure 3A:
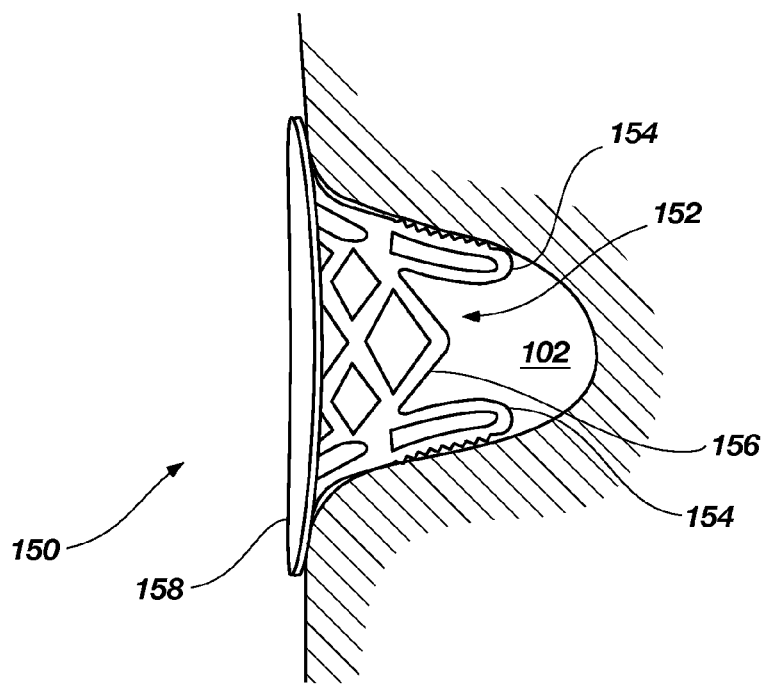
FIG. 3A illustrates a medical device according to another embodiment of the present invention.
Figure 3B:
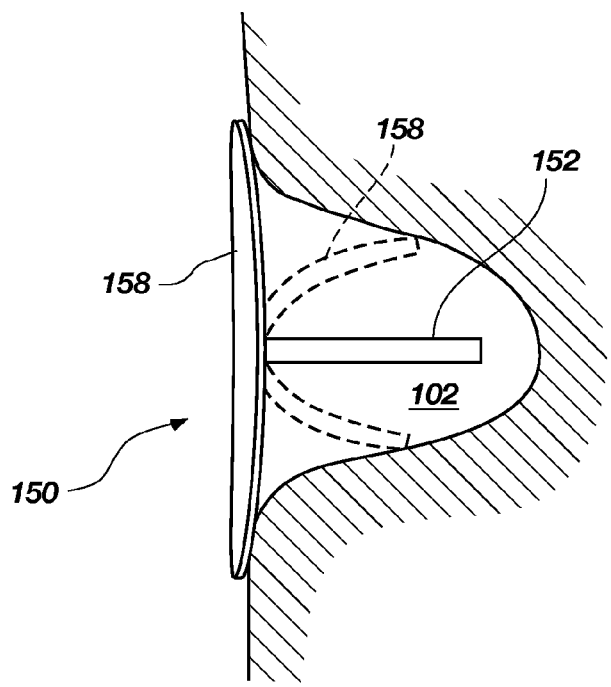
FIG. 3B shows the medical device of FIG. 3A disposed in an atrial appendage according to an embodiment of the present invention.

FIGS. 3A and 3B illustrate another embodiment of a medical device 150 configured to engage and be anchored within an LAA 102 (see also FIG. 1C) and occlude the opening 114 of the LAA 102. The medical device 150 includes a planar structure 152 having distal anchors 154 extending from a multi-cellular central portion 156 that is attached to a cover member 158. The cover member 158 may include, for example, a polymer substrate. The medical device 150 is similar to the embodiment described with respect to FIGS. 2A-2C, except the medical device 150 only employs a single planar structure 152. The planar structure 152 of the medical device 150 (or the planar structures 132A and 132B of the previously described medical device 130) may be formed, for example, in a manner similar to the planar structures described in U.S. patent application Ser. No. 11/836,123 filed on Aug. 8, 2007, entitled METHODS, SYSTEMS, AND DEVICES FOR REDUCING THE SIZE OF AN INTERNAL TISSUE OPENING and assigned to the assignee hereof, the disclosure of which is incorporated by reference herein in its entirety.

The cover member 158 may be sized and configured to be biased or to sit against the LAA opening 114. Further, as with other embodiments, the cover member 158 is not limited to a polymer substrate, but may include any suitable tissue in-growth member known in the art. Additionally, with reference to FIG. 3B, which shows a rotated view of the medical device 150 as compared to that of FIG. 3A, the cover member 158 may be positioned within the LAA 102 so as to fold distally (as shown in dashed lines) and against the LAA wall 112. In another embodiment multiple cover members 158 may be used with one folded within the LAA 102 and another covering the opening 114.

Figure 4:
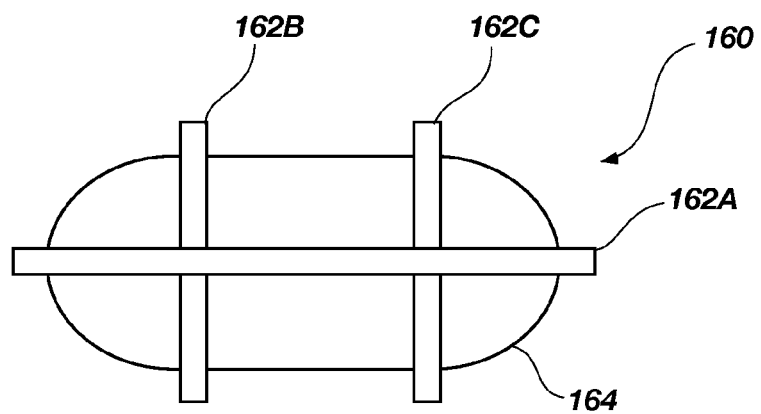
FIG. 4 is an end view of a medical device according to an embodiment of the present invention.

FIG. 4 shows an end view of another medical device 160 according to an embodiment of the present invention. The medical device is similar to that which is described with respect to FIGS. 2A through 2C having a plurality of planar structures 162A, 162B and 162C coupled with a cover member 164. The cover member 164 exhibits a different size and shape than that of the medical device 130 of FIGS. 2A-2C. Additionally, to compliment the elongated geometry of the cover member 164, one of the planar structures 162A is also elongated and multiple planar structures 162B and 162C are associated with the elongated planar structure 162A to extend out-of-plane (e.g. orthogonally) with respect to the elongated planar structure 162A. With the anchoring system having multiple flat or planar structures, it can provide additional support and anchoring to the LAA wall 112 to prevent migration of the device. Additionally, this configuration enables closure of an LAA 102 (FIG. 1C) that, for example, is relatively large or exhibits an elongated opening.

Figure 5:
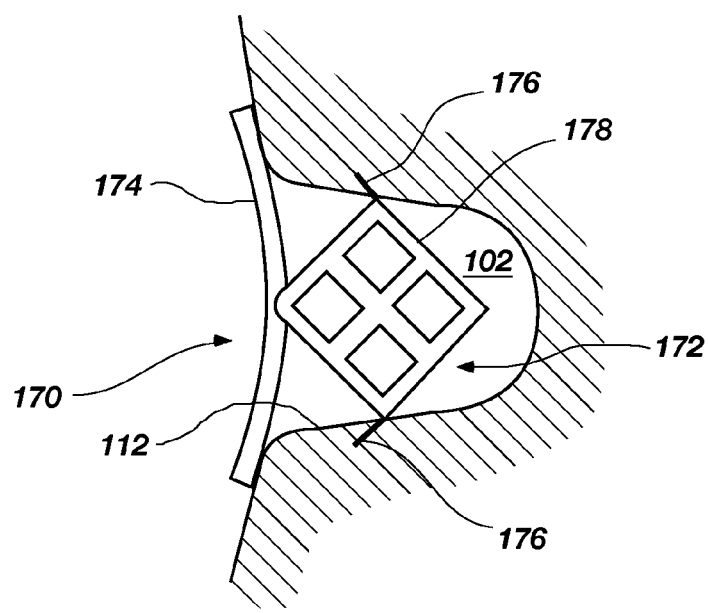
FIG. 5 is a side view of a medical device disposed in an atrial appendage according to an embodiment of the present invention.

Referring now to FIG. 5, another medical device 170 is shown. The medical device 170 is generally similar to that which is described with respect to FIGS. 3A and 3B and includes a planar structure 172 coupled with a cover member 174. However, rather than using anchors that extend distally within the LAA 102 (as described with respect to FIGS. 3A and 3B), anchors 176 are coupled to the central portion 178 of the planar structure 172 so as to extend back towards the cover member 174 and into the flesh of the LAA wall 112.

Figure 6A:
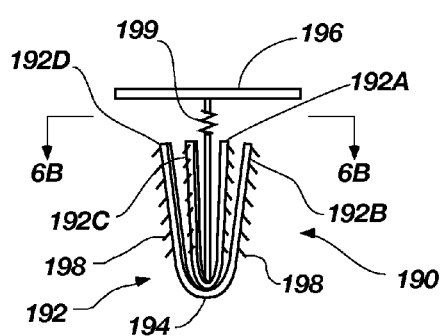
FIGS. 6A and 6B illustrate respective side and end views of a medical device according to another embodiment of the present invention.
Figure 6C:
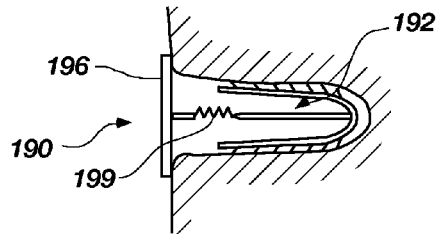
FIG. 6C shows the medical device of FIGS. 6A and 6B disposed in an atrial appendage.
Figure 6B:
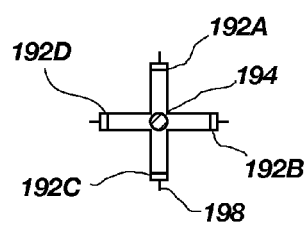

Referring now to FIGS. 6A through 6C, another embodiment of medical device 190 is shown. In this embodiment, the medical device 190 includes a multi-arm anchor 192 coupled with a cover member 196. As with the other embodiments described herein, the cover member 196 may include a suitable tissue in-growth material to promote or enhance growth of tissue into and over the cover member 196.

The anchor 192 includes a plurality of arms 192A-192D joined at a central hub 194. Along the length of each arm 192A-192D, tines 96 may extend therefrom and be oriented so that the medical device 190 is substantially prevented from migrating from the LAA 102 once it is disposed therein. The arms 192A-192D may each extend from the central hub 194 and self-expand when delivered to the LAA 102 in a manner such that each arm 192A-192D independently expands and biases against the LAA wall 112 to secure the medical device 112 within the LAA 112. A biasing member 199 may be coupled between the anchor 192 and the cover member 196 so as to bias the cover member 196 against the atrial wall 124 and more effectively cover or occlude the LAA opening 114.

Figure 7:
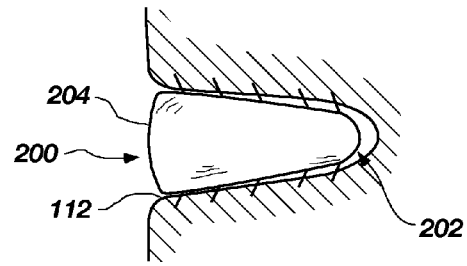
FIG. 7 shows another embodiment of a medical device disposed in an atrial appendage.

FIG. 7 illustrates an embodiment of a medical device 200 that includes an anchor 202 similar to that described with respect to FIGS. 6A through 6C. The medical device 200 of this embodiment includes a foam or fabric 204 disposed over the proximal ends of the anchor 202. In one embodiment, the foam or fabric 204 may be configured to substantially fill or cover the envelope defined by the geometry of the expanded anchor 202. Similar to previously described embodiments, tines 206 may be associated with the anchor 202 to engage the LAA wall 112.

Figure 8:
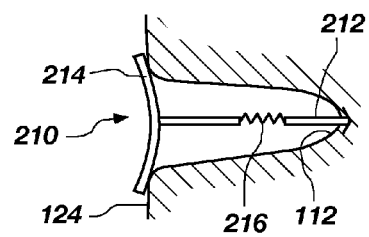
FIG. 8 shows another embodiment of a medical device disposed in an atrial appendage.

FIG. 8 illustrates another embodiment of a medical device 210 having an anchor 212 coupled to a cover member 214 via a biasing member 216. The anchor 212 may include a distal end portion 218 configured to be connected to the LAA wall 114 such as by tines or barbs 220 or by stitching. Similar to previous embodiments, cover member 214 can, thereby, be biased against the left atrial wall 124 so as to cover the LAA opening 114. Again, the cover member 214 may include an in-growth material, such as a polymer substrate.

Figure 9A:
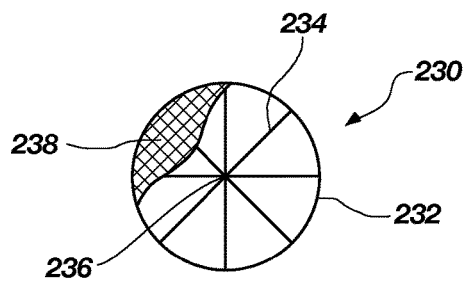
FIG. 9A is an end view of a medical device according to another embodiment of the present invention.
Figure 9B:
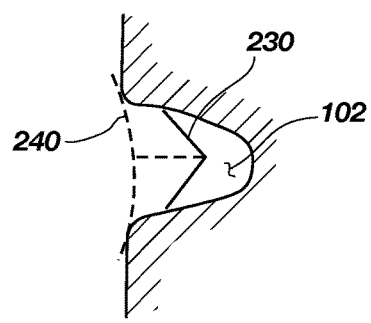
FIG. 9B shows the medical device of FIG. 9A disposed in an atrial appendage according to one embodiment of the present invention.

Referring now to FIGS. 9A and 9B, a medical device 230 is shown that includes a self-expanding frame structure 232 having a plurality of spokes 234 joined at a common hub 236. The self-expanding feature of the frame structure 232 can assist or substantially ensure that the medical device 230 is secured within the LAA 102 by exerting an appropriate radial force against the LAA walls 114. An in-growth material 238 (only partially shown for purposes of clarity), which may include a polymer substrate such as foam or fabric, may extend around the frame structure 232 to promote tissue growth and, thereby, close the opening 114 of the LAA 102. As shown in FIG. 9B, the frame structure 232 may act to close the LAA 102 on its own accord, or it may be used in conjunction with a separate cover member 240 (shown in dashed lines) and act as an anchoring device (or as a redundant closure device) associated with such a cover member 240.

Figure 10A:
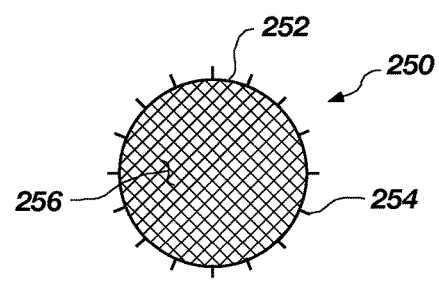
FIGS. 10A and 10B are end and cross-sectional views of a medical device according to an embodiment of the present invention.
Figure 10B:
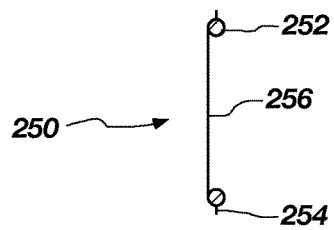
Figure 10C:
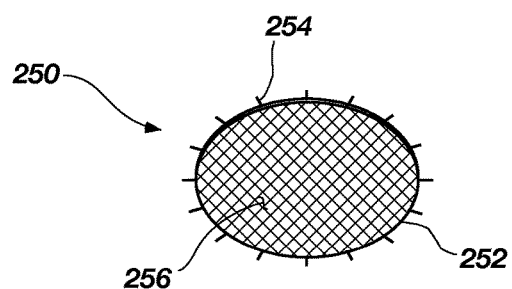
FIG. 10C shows a variation of the embodiment shown in FIGS. 10A and 10B.
Figure 10D:
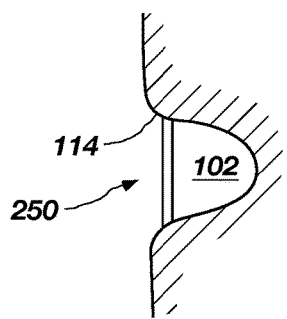
FIG. 10D shows the medical devices of FIGS. 10A-10C disposed in an atrial appendage according to another embodiment of the present invention.

FIGS. 10A through 10D illustrate a medical device 250 having a self-expanding frame structure 252 that expands in a radial direction so as to engage the walls 114 of an LAA 102. The frame structure 252 can be substantially planar or flat and can be a continuous or unitary structure. The frame structure 252 may exhibit any of a variety of geometric configurations when it is in an expanded state. For example, the frame structure may exhibit a circular geometry as indicated in FIG. 10A, or it may exhibit a substantially oval geometry as indicated in FIG. 10C. The frame structure 252 may exhibit any other suitable peripheral shape that enables the frame structure 252 to expand and cause associated tines 254, extending from the periphery of the frame structure 252, to grab or engage the LAA wall 114 as indicated in FIG. 10D. A polymer substrate 256 (or any suitable tissue growth promoting member) may be attached to the frame structure 252. For example, the material of such a substrate 256 may wrap around and encase the frame structure 252, it may extend between opposing peripheral sides of the frame structure 252, or it may do both. In another embodiment, the medical device may be devoid of tines such that it relies solely on a radially expanding force of the frame structure 252 to maintain medical device within the LAA 102.

Figure 11:
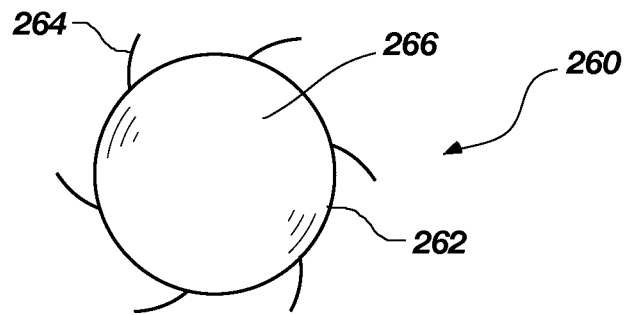
FIG. 11 is an end view of a medical device according to yet another embodiment of the present invention.

FIG. 11 illustrates another embodiment of a medical device 260 to be disposed and anchored within an LAA 102 (FIG. 1C). The medical 260 may include a self-expanding frame member 262, that may exhibit a flat configuration with a rounded or arcuate periphery when in an expanded state, with tines 264 configured to anchor within the LAA wall 114. The tines 264 are curved such that they do not extend directly radially outward from the frame member 262. Such a configuration enables the medical device 260 to engage the LAA wall 114 by rotating the expanded medical device 260 within the LAA 102 to effectively lodge the tines within the LAA wall 114. One advantage of rotating the device to effect anchoring thereof is that the device is anchored without having to pull the device in the proximal direction to effect such anchoring. The medical device 260 may further include a polymer substrate 266 or other in-growth material to act as a cover member and effect tissue growth when disposed within the LAA 102. In another embodiment, the frame member 262 could act as an anchor member for a separate cover member such as has been described hereinabove.

Figure 12:
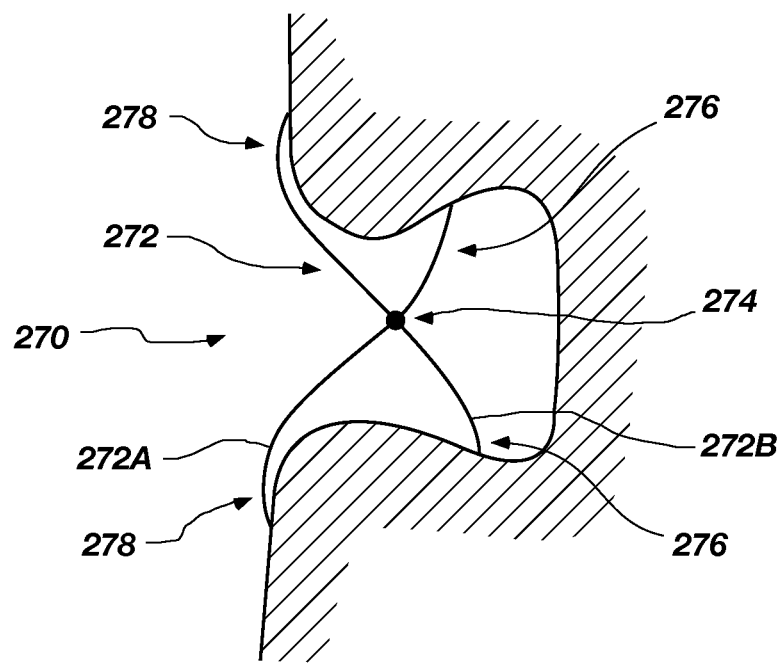
FIG. 12 shows a medical device according to another embodiment of the present invention disposed in an atrial appendage.

FIG. 12 illustrates another embodiment of a medical device 270. The medical device includes a frame member 272 having multiple elongate members 272A and 272B that are configured to bypass or cross each other at an intermediate portion 274 of each elongate member 272A and 272B. The frame member 272 can be self-expanding and, when in the expanded configuration, each elongate members 272A and 272B may expand to a curvilinear configuration such that the multiple elongate members cooperate to collectively exhibit a geometry in the shape of an hour glass. From a common juncture (i.e., the intermediate portion 274 of the multiple elongate members 272A and 272B), there are distally extending portions 276 and proximally extending portions 278 of the elongate members 272A and 272B that form the hour glass configuration. The distally extending portions 276 can act as distal anchor portions. The proximally extending portions 278 can act as proximal anchor portions and a support structure for a proximal cover portion (not shown in FIG. 12). As in the previous embodiments, the frame member 272 can include an in-growth member, such as a polymer substrate, to act as a cover and/or to promote or induce tissue growth.

Referring now to FIGS. 13A through 13E (and continued reference to the LAA shown in FIG. 1C), various embodiments of another medical device 280 are shown. As seen in FIGS. 13A through 13C, the medical device 280 may include a frame member 282 formed to exhibit the shape of a helical coil. FIG. 13A shows and end view of the medical device 280 while FIG. 13B shows a side view of the medical device 13B.

The frame member 282 may be formed from, for example, a shape member alloy such as Nitinol, such that the frame member 282 may be disposed within a catheter 284 or other delivery vehicle in an undeployed (e.g., a lengthened, uncoiled) state. When deployed from the catheter 284 or other delivery vehicle, the frame member 282 expands to its coiled state such as shown FIGS. 13A-13C. When in the expanded, coiled state, the frame member 282 may be sized to engage the LAA wall 112 and apply a desired force to anchor or lodge the medical device 280 within the LAA 102. While not expressly shown in FIGS. 12A-13C, the frame member 282 may be coupled to a cover member, such as been described with respect to numerous other embodiments herein, to cover or occlude the LAA opening 114.

In another embodiment, and as shown in FIGS. 13D and 13E, the frame member 282 may be coated or encased with a foam or other tissue in-growth material 286. Depending on the thickness of the coating of such material on the frame member 282, and depending on the radius and spacing of the coils of the frame member 282, such a configuration may act as an occluding member due to the collection or accumulation of the in-growth material on and within the coils of the frame member 282. In yet other embodiments, the frame member need not be in the configuration of a helical coil. Rather, for example, it may for a substantially circular geometry or oval geometry such as are exhibited by the embodiments described with respect to FIGS. 10A-10D. In other embodiments, the frame member may be a coil which is substantially flat or lies within a single plane. Other geometric configurations are also contemplated.

Figure 14:
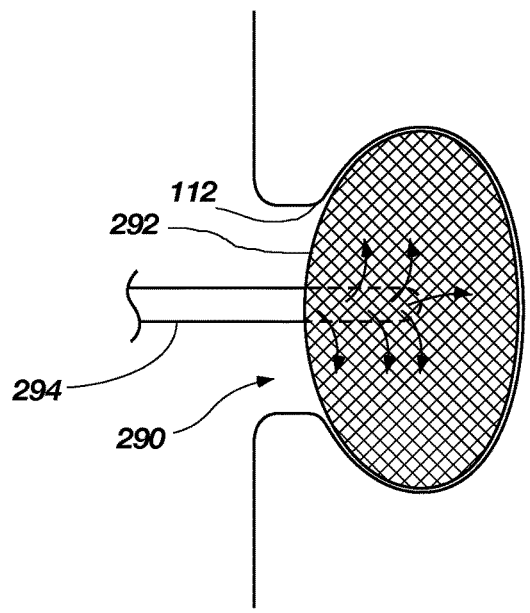
FIG. 14 shows a medical device disposed in an atrial appendage according to yet another embodiment of the present invention.

FIG. 14 illustrates another embodiment of a medical device 290 configured to be disposed within and fill or occlude the LAA 102 (FIG. 1C). The medical device 290 includes a foam body 292 that is sized and configured such that, when deployed within the LAA 102, the LAA 102 expands to a size that is larger than its natural state. After the foam body 292 is disposed within the LAA 102, a stiffener material may then be released from a catheter 294 and injected throughout the foam body 292 to cause the foam body 292 to become substantially rigid or stiff. The foam body may be anchored within the LAA by virtue of the forces applied to the LAA wall 112, by its rigidity, or through a combination of both properties. Although not shown, the medical device 280 may also include a cover member to further prevent potential embolic material from migrating from the LAA 102.

Figure 15:
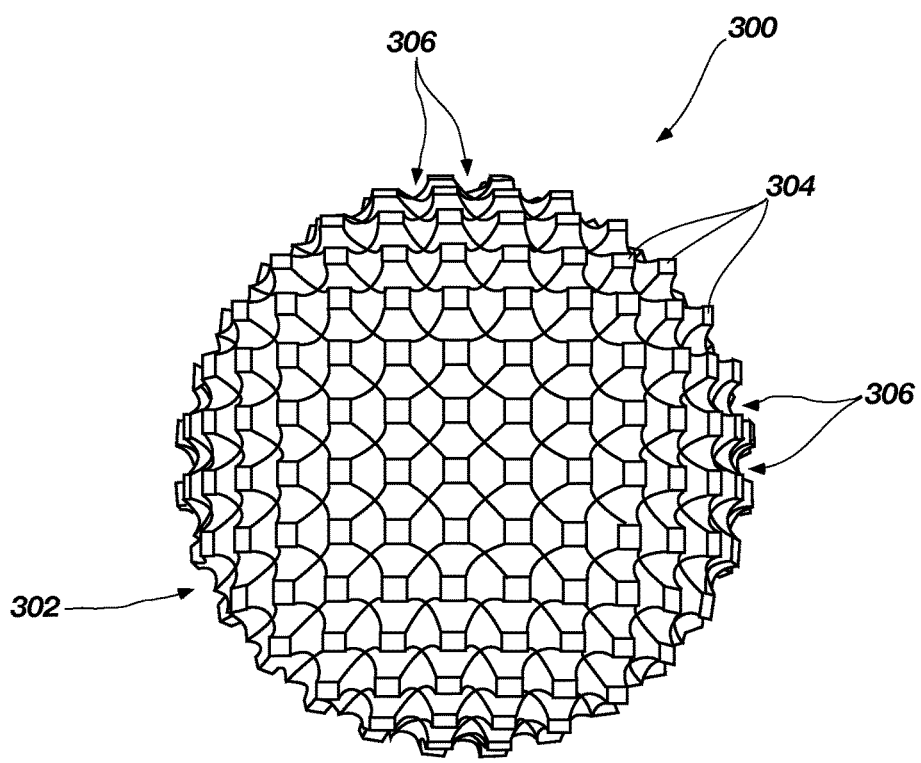
FIG. 15 shows a medical device in the general form of a substantially spherical body according to one embodiment of the present invention.

Referring now to FIG. 15, another medical device 300 is shown. The medical device 300 includes a body 302 which may exhibit a substantially spherical geometry and have a textured surface. The textured surface may include a plurality of protruding portions 304 (which may exhibit any of a variety of shapes) separated by recessed portions 306. In one embodiment of the present invention, the body 302 includes a self-expanding resilient porous material that, when fully expanded, enlarges to a predetermined expanded shape. The body 302 may be formed, for example, of a foam material. For example, the body may be formed a polyurethane material, a polymer foam, or a polyvinyl acetate material, silicon material, or polyester material. Other polymeric materials that can be utilized are self-expanding felts. In the case of foam, such foam may be a reticulated foam, typically undergoing a heating process to open the pours within the foam as known in the art. The foam may also be a non-reticulated foam.

It is also contemplated that the body 302 of the medical device 300, in another embodiment, can be formed without the plurality of protruding portions and recessed portions described above. In other words, the surface of the body 302 can be left relatively smooth or untextured in its substantially natural state of, for example, the foam material.

In one embodiment, the body may be a "solid" geometry meaning that the foam or other material extends through the body 302. In another embodiment, the body 302 may be substantially hollowed out or hollowed at one or more selected portions within the body 302. When hollowed out, the body 302 would be more compact when collapsed and carried by a catheter or other delivery vehicle. While the body 302 may exhibit other geometries (e.g., cylindrical, ovoid, elongated), the use of a spherical or substantially spherical geometry (referring to the overall shape and disregarding the textured surface) enables deployment of the medical device 300 within an LAA 102 (FIG. 1C) with less sensitivity to the approach angle of the catheter or other delivery vehicle with respect to the LAA 102. Thus, use of a substantially spherical configuration provides greater ease of use in installing or deploying the medical device 300. Other configurations may also be employed, such as conical, cylindrical or combinations thereof, which also may include hollowed out portions.

In another embodiment, the foam or other material can include variations within portions of the body 302 such that various portions of the body may compact smaller than other portions of the body. Such can be employed, for example, by manipulating the number of pours per square inch in the material forming the body 302 so that the body exhibits a graded porosity. For example, for a spherical configuration, the central region of the foam body may include a different number of pours than the outer regions of the foam body so as to manipulate the compactive and expansive characteristics of the foam body. Additionally, or alternatively, one-half of the sphere may exhibit one level of porosity while the other half exhibits a different level of porosity. Similarly, along the length of any other shaped configuration, such as a conical or cylindrical configuration the level of porosity may change. Additionally, such changes in porosity may be gradual, or may be relatively abrupt.

Figure 16A:
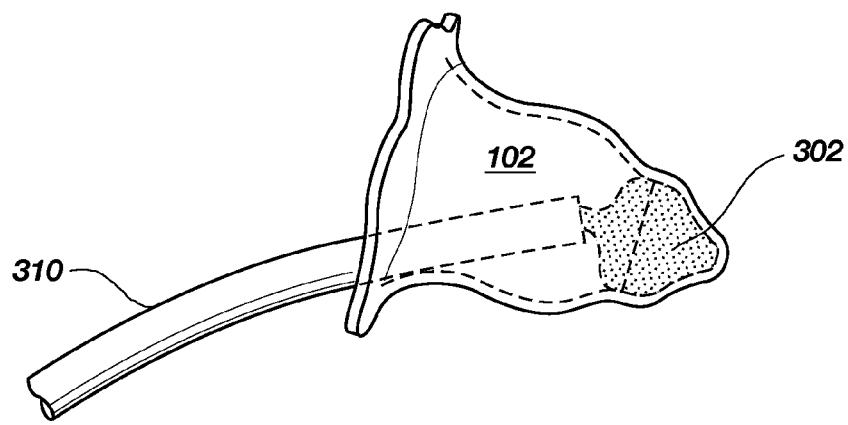
FIGS. 16A-16C show the medical device of FIG. 15 being deployed into an atrial appendage according to an embodiment of the present invention.
Figure 16B:
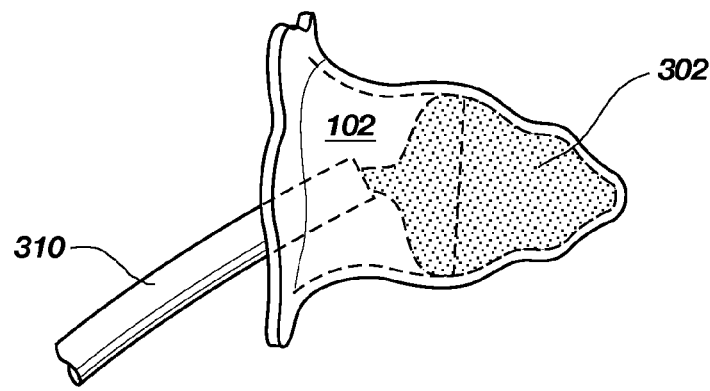
Figure 16C:
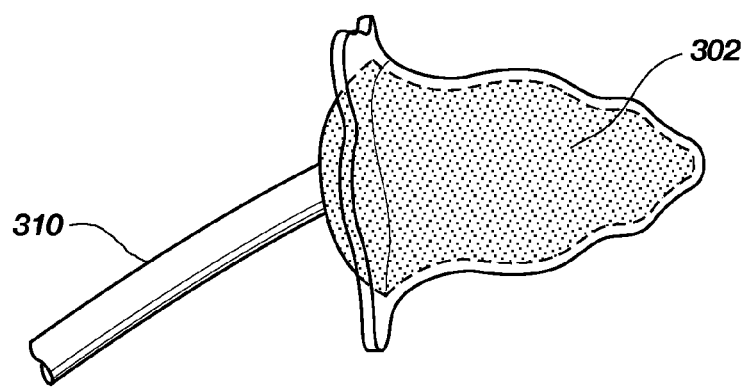
Figure 16D:
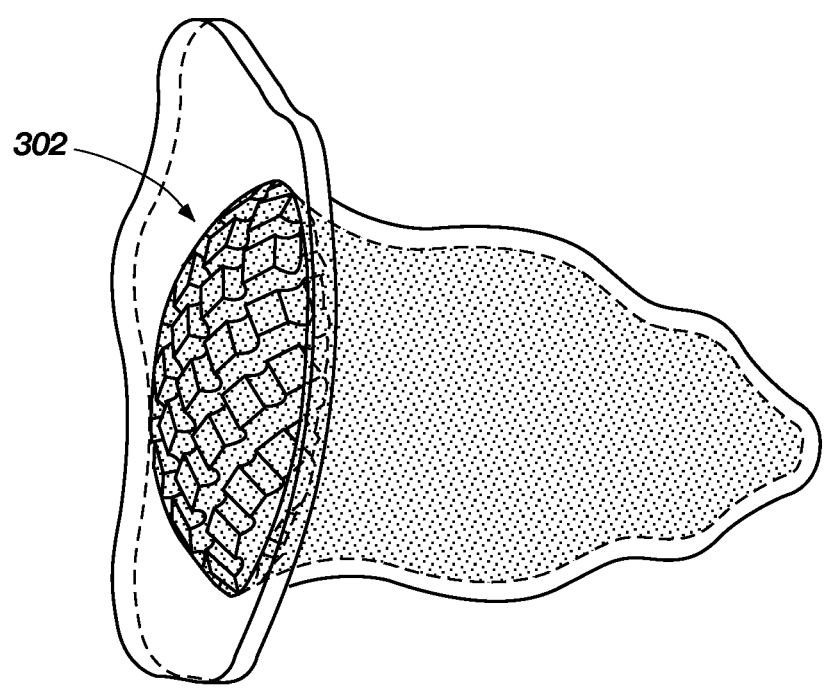
FIG. 16D shows the medical device of FIG. 15 disposed in an atrial appendage.

Referring to FIGS. 16A through 16D, deployment of the medical device 300 is shown. As seen in FIG. 16A, a catheter 310 or other delivery vehicle is guided to the LAA 102 using techniques that will be appreciated and understood by those of ordinary skill in the art. The catheter 310 enters the LAA 102 and begins to deploy the body 302 from within the catheter 310. As seen in FIGS. 16A-16C, as the medical device is deployed from the catheter 310, it expands (the body 302 being formed of a self-expanding material) so as to fill or substantially fill the LAA 102. In other embodiments, the body 302 may simply fill enough of the LAA 102 to anchor itself within the LAA 102 and to block or occlude the LAA opening 114. FIG. 16D shows the medical device disposed within the LAA 102.

The textured surface of the body 302 may be tailored depending on a variety of factors. For example, the protruding portions 304 may be configured to effect increased engagement with the LAA wall 114 (FIG. 1C) and help anchor the medical device 300 within the LAA 102. Additionally, the depth, width and frequency of the recessed portions 306 of the textured surface may be configured to cooperatively engage with trabeculations within the LAA 102. Further, the textured surface may have portions that are selectively configured for a specific function as will be discussed in further detail below.

Figure 17A:
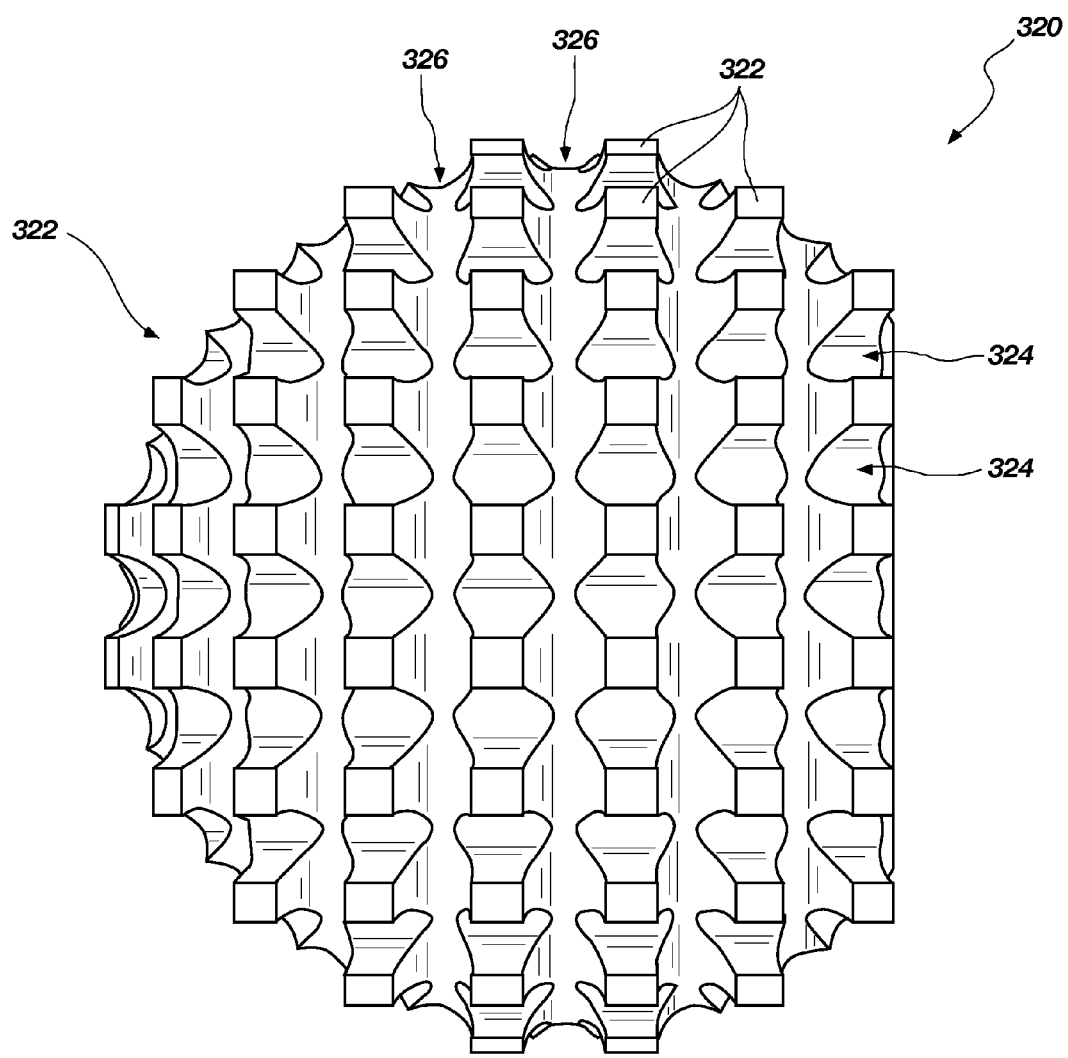
FIGS. 17A and 17B are side and end views of another medical device according to an embodiment of the present invention.
Figure 17B:
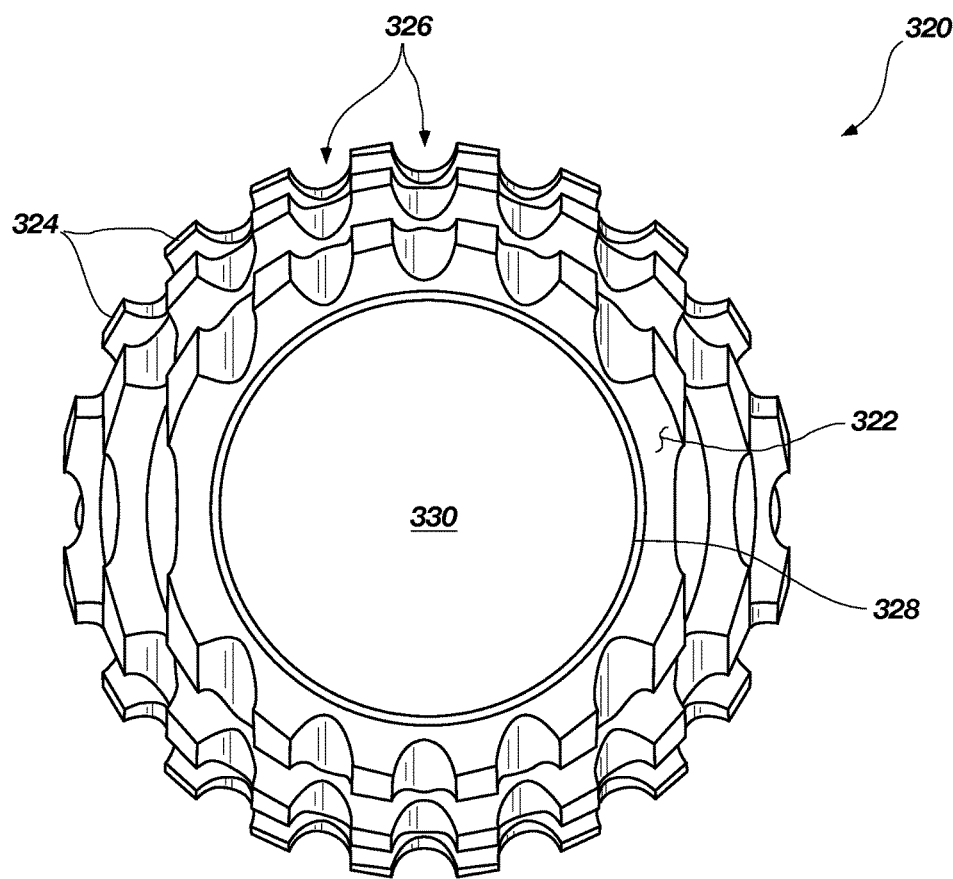

Referring briefly to FIGS. 17A and 17B, another embodiment of a medical device 320 is shown. The medical device 320 is similar to that which is described with respect to FIG. 15 and includes a body 322 have a textured surface with protruding portions 324 separated by recessed portions 326. The body 322, while exhibiting a generally spherical geometry, is truncated on one side to define an opening 328 that exposes the hollow interior 330 of the body 322. The opening 326 does not impair the functionality of the medical device to occlude the LAA opening 114 (FIG. 1C) so long as the opening 328 is positioned such that it is fully within the LAA 102 and not directly exposed to the LAA opening. In other words, the opening should be positioned so as to not create a communication path between the atria and the LAA 102. Such a configuration further reduces the overall mass of the body 302 making it smaller when compacted within a catheter or other delivery mechanism. Additionally, such a configuration may be easier to manufacture when using certain manufacturing processes as will be appreciated by those of ordinary skill in the art.

Figure 18A:
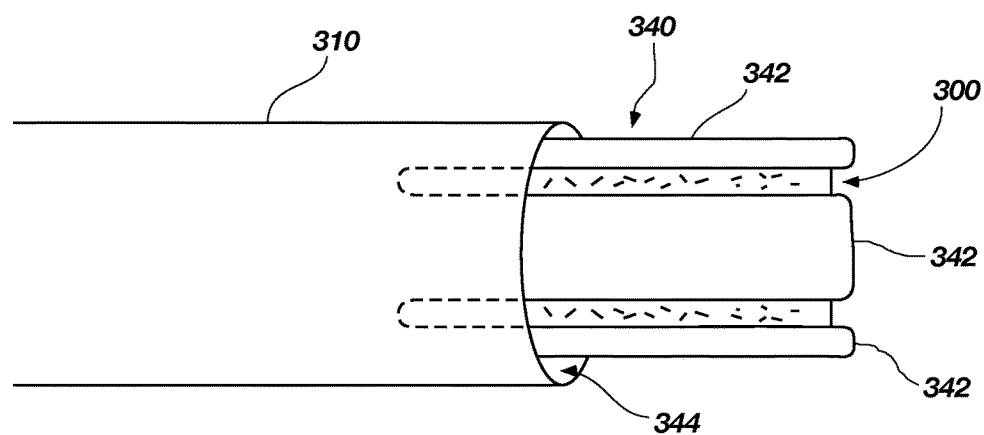
FIG. 18A shows a delivery mechanism or apparatus for deploying a medical device in accordance with an embodiment of the present invention.
Figure 18B:
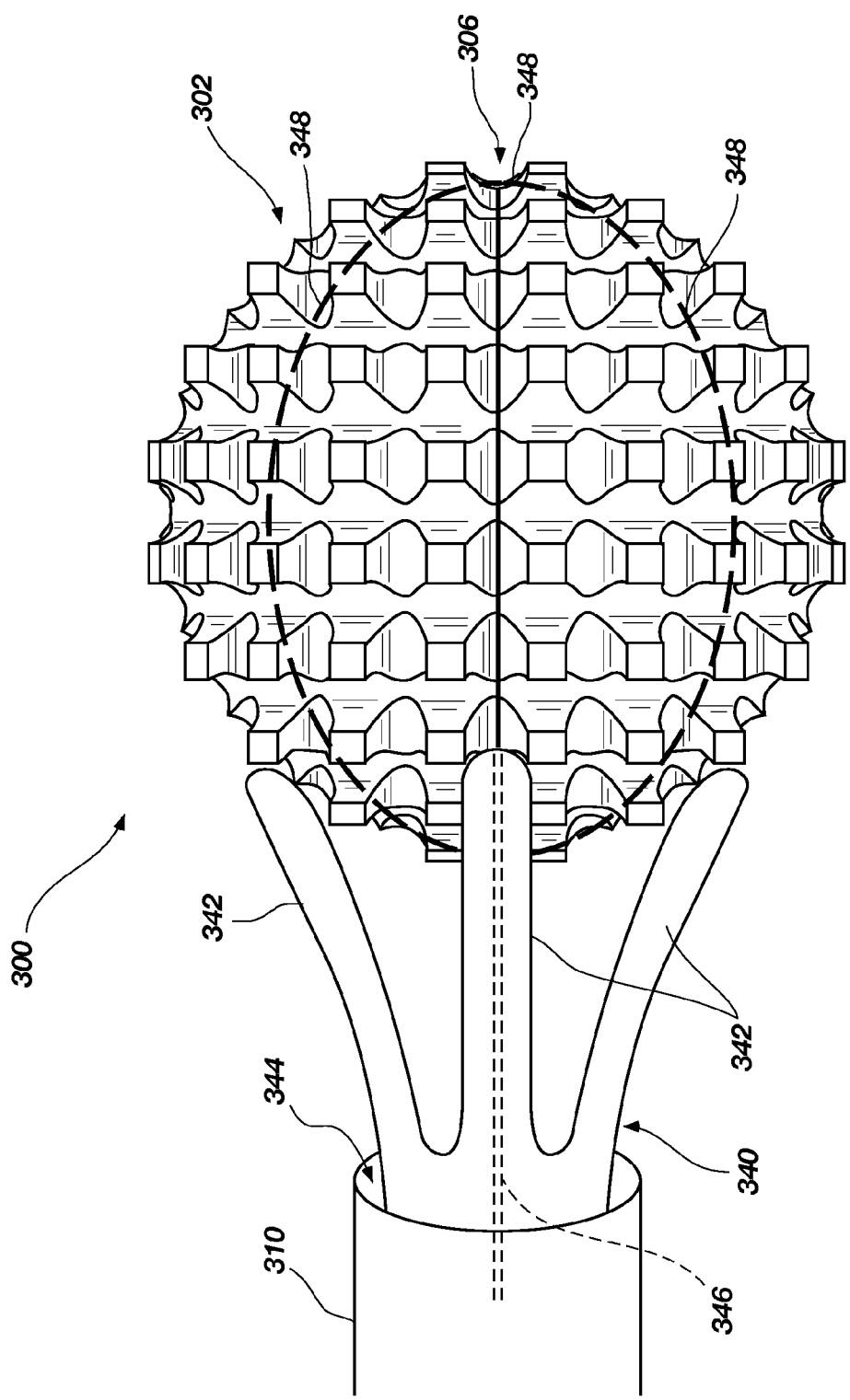
FIG. 18B shows the delivery mechanism of FIG. 18A deploying the medical device of FIG. 15.

Referring now to FIGS. 18A and 18B, delivery and recapture of the medical device 300 described with respect to FIG. 15 is described. The medical device 300 is collapsed and retained within a slotted sleeve 340 associated with the catheter 310. The slotted sleeve 340 includes multiple fingers or elongated members 342 having free ends. The catheter 310 is guided to the LAA 102 (FIG. 1C) using techniques familiar to those of ordinary skill in the art. When the catheter 310 is in position for delivery of the medical device 300, the slotted sleeve 340 extends longitudinally out from an opening of the catheter 310. The fingers or elongated members 342 are configured to radially expand (due to self expansion, expansion due to the force applied by the medical device 300, or both), and the medical device is released from the slotted sleeve 342.

As will be appreciated by those of ordinary skill in the art, it is sometimes necessary to recapture the medical device 300 after deployment for purposes of repositioning the medical device within the LAA 102. In such a case, a tether 346 may be coupled to a plurality of ties 348 that circumscribe the body 302 of the medical device. The tether 346 and the web or cage formed by the ties 348 pull the medical device 300 back within the envelope defined by the radially expanded fingers 342 of the slotted sleeve 340. As the tether 346 and slotted sleeve 340 are drawn back in through the opening 344 of the catheter 310, the medical device 300 is returned to a collapsed state within the catheter 310 and may be redeployed into the LAA or removed completely from the patient. When the device 300 is satisfactorily position with the LAA 102, the tether may be disconnected from the ties 348.

In one embodiment, such ties 348 may be formed of a shape memory alloy, such as Nitinol, to assist in expansion of the medical device 300 in expanding when deployed in the LAA. The ties 348 may be disposed within recesses 306 of the medical device's textured surface. When deployed in an LAA 102, the ties 348 may remain with the body 302, although they may not be intended to serve any specific purpose in terms of anchoring the medical device 300 or promoting tissue growth. In another embodiment, instead of using ties 348 for recapture purposes, a mesh bag may be disposed about the body 302 of the medical device 300 in a manner similar to a further embodiment that is described hereinbelow.

In yet another embodiment, the slotted sleeve 340 need not be utilized. Instead, a pusher element (e.g., a rod or other device) may be inserted through the body 302 and configured to engage the distal end of the body 302. When it is desired to recapture the medical device 300, the pusher element may push against the distal end of the body while the ties are pulled toward the catheter 310 to effect an elongation (and a corresponding radial contraction) of the body 302. The medical device may then be drawn back within the catheter 310.

Figure 19A:
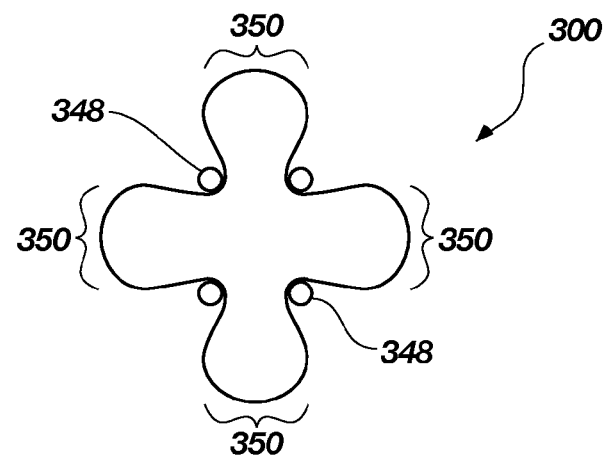
FIGS. 19A and 19B are end views of a medical device while in a compressed, pre-delivery state and an expanded, post-delivery state according to an embodiment of the present invention.
Figure 19B:
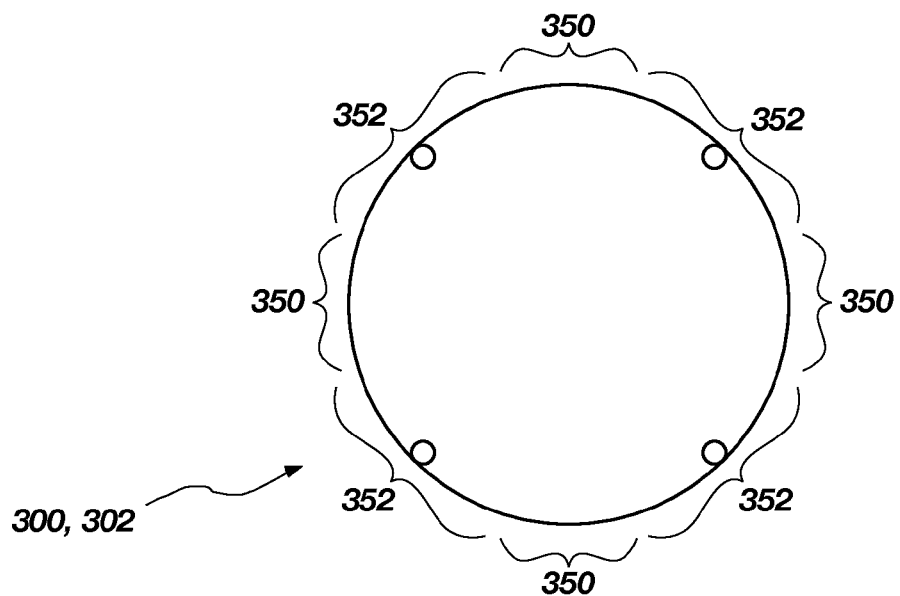

Referring now to FIGS. 19A and 19B, schematics are shown of a medical device 300 in a collapsed state (i.e., when in a catheter or other delivery vehicle), and an expanded state, respectively. Collapse of the medical device 300 may be assisted by ties 348 such as have been described above in terms of retaining the body 302 in a relatively compact form. When the medical device 300 is in a collapsed state, certain portions of its outer surface are in contact with the delivery vehicle. These areas are referred to herein as delivery contact surfaces and are generally indicated by reference numeral 350. It may be desirable to reduce the friction between these delivery contact surfaces 350 and the delivery vehicle. Thus, in certain instances, the size and shape of the protrusions 304 may be selectively tailored for such delivery contact surfaces 350.

In yet another embodiment, the protrusions 304 in the contact surface areas 350 may exhibit similar geometric configurations as the rest of the texture surface of the body 302. However, the surface areas not in contact with delivery vehicle (referred to as delivery non-contact surface indicated by reference numerals 352) may be modified by stiffening the material or further roughening the surface of the protrusions 304. For example, such delivery non-contact areas may be coated or metalized, such as with graphite, to stiffen the protrusions 304 and provide a roughened surface area. These coated areas then provide improved engagement of the medical device 300 with the LAA wall 114 (FIG. 1C) when deployed in the LAA 102. Such coating or metallization can also serve another purpose to provide radio opacity for imaging purposes. Materials that can be used for such coating can be tungsten, platinum, gold or titanium or any other materials known in the art to provide radio opacity.

Figure 20A:
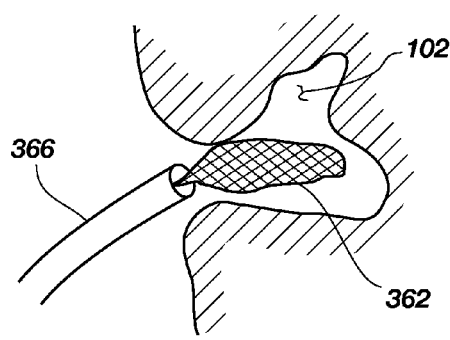
FIGS. 20A-20D show a medical device and a delivery system at various stages of deployment according to another embodiment of the present invention.
Figure 20B:
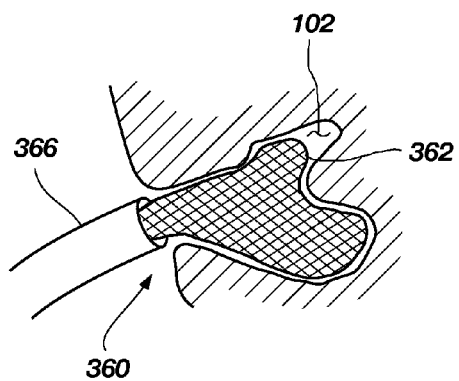
Figure 20C:
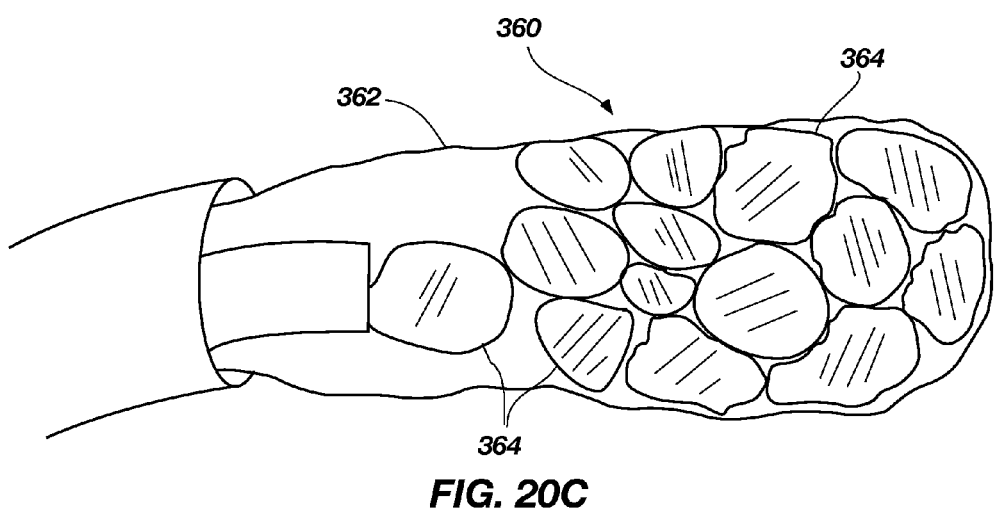
Figure 20D:
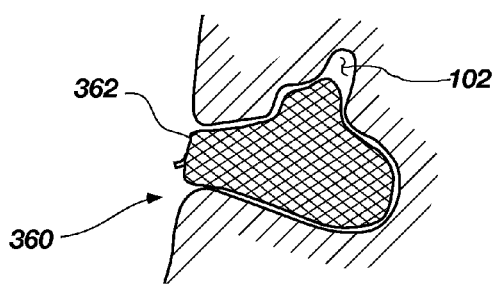

Referring now to FIGS. 20A through 20D, a medical device 360 according to another embodiment of the present invention is described. The medical device 360 includes a mesh bag 362 and a plurality of self-expanding bodies 364, such as foam bodies. The mesh bag 362 may be formed, for example, from nylon, polyester, knitted fiber, or some other appropriate material. In another embodiment, the bag 362 may be formed as a molded silicone material. As shown in FIG. 20A, the mesh bag 362 is delivered from a catheter 366 or other delivery mechanism into the LAA 102. Individual, self-expanding bodies 364 are then disposed into the mesh bag 362 from a separate sleeve or lumen of the catheter 366 as shown in FIGS. 20B and 20C. The expansion of the self-expanding bodies 364 stretches the mesh bag 362 such that the medical device 360 substantially conformally fills the LAA 102. Once the LAA is filled, the mesh bag 362 is tied off or otherwise securely closed to retain the self-expanding bodies 364 within the bag 362 and the LAA 102.

Use of a mesh bag 362 and multiple self-expanding bodies 364 again provides ease of use for the doctor deploying the medical device due to the fact that deployment is relatively insensitive to the approach angle of the catheter 366. Additionally, the use of multiple smaller expanding bodies 364 makes it more likely to substantially fill the LAA 102 in a generally conformal manner.

Various other features may be included in any of the above described embodiments. For example, radio opaque markers may be associated with any of a variety of components of the described medical devices to facilitate monitoring of the deployment and positioning of the medical device. Additionally, various materials may be used including bioresorbant materials for certain components. Further, various components may be coated to effect a desired biological reaction as will be appreciated by those of ordinary skill in the art.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description.

What is claimed is:

1. A medical device for modifying a left atrial appendage (LAA), comprising:
   a frame member including distal anchor members for anchoring the frame member within the LAA, the frame member including a unitary, seamless central portion having a plurality of struts defining a multicellular structure extending between and configured to self-expand and directly bias the distal anchor members against a wall in the LAA, the plurality of struts and the distal anchor members extending in a common plane; and a tissue growth member attached to the frame member and configured to occlude an opening of the LAA;

wherein the distal anchor members comprise first and second distal anchor members extending in a first plane and third and fourth distal anchor members extending in a second plane, the first plane transverse to the second plane.

2. The medical device of claim 1, wherein the distal anchor members comprise a first distal anchor portion and a second distal anchor portion with the central portion extending therebetween.

3. The medical device of claim 1, wherein the distal anchor members comprise tines extending therefrom for engaging the wall in the LAA.

4. The medical device of claim 1, wherein the frame member comprises proximal anchor members extending from the central portion.

5. The medical device of claim 4, wherein the tissue growth member is directly attached to the proximal anchor members.

6. The medical device of claim 1, wherein the multi-cellular structure of the central portion extends with a substantially flat configuration.

7. The medical device of claim 6, wherein the tissue growth member comprises a polymeric substrate.

8. A medical device for modifying a left atrial appendage (LAA), comprising:

a frame member including a central portion having a plurality of struts defining a multi-cellular structure and an anchoring system, the plurality of struts and the anchoring system extending in a common plane, the plurality of struts extending between and configured to self-expand and directly bias the anchor system to anchor the frame member at least partially within the LAA; and a tissue growth member attached to the frame member; wherein the anchoring system comprises:

a first distal anchor and a second distal anchor, the first distal anchor being co-planar with the second distal anchor; and a third distal anchor and a fourth distal anchor, the third distal anchor being co-planar with the fourth distal anchor, the first distal anchor extending in a discrete plane relative the third distal anchor.

9. The medical device of claim 8, wherein the multi-cellular structure of the central portion extends with a substantially flat configuration.

10. The medical device of claim 8, wherein the frame member comprises proximal anchor members extending from the central portion.

11. The medical device of claim 10, wherein the tissue growth member is attached to the proximal anchor members.

12. The medical device of claim 8, wherein the distal anchor members comprise tines extending therefrom for engaging the wall in the LAA.

13. The medical device of claim 8, wherein the central portion is a unitary and seamless structure.

* * * * *